United States Patent [19]

Hamersly

[11] Patent Number: 5,683,353

[45] Date of Patent: *Nov. 4, 1997

[54] ADJUSTABLE FLEXION AND EXTENSION JOINT ORTHOSES

[75] Inventor: Greg A. Hamersly, Atascadero, Calif.

[73] Assignee: DeRoyal/LMB, Inc., San Luis Obispo, Calif.

[*] Notice: The term of this patent shall not extend beyond the expiration date of Pat. No. 5,472,410.

[21] Appl. No.: 564,481

[22] Filed: Nov. 29, 1995

Related U.S. Application Data

[63] Continuation of Ser. No. 231,131, Apr. 22, 1994, Pat. No. 5,472,410.

[51] Int. Cl.$^6$ ........................................................ A61F 5/00
[52] U.S. Cl. ............................ 602/16; 602/20; 602/26; 601/33
[58] Field of Search .................................. 601/23, 33, 34, 601/40; 602/5, 16, 20–23, 26; 482/44–47, 122, 124

[56] References Cited

U.S. PATENT DOCUMENTS

| | | |
|---|---|---|
| Re. 33,621 | 6/1991 | Lamb et al. |
| 288,239 | 11/1883 | Ingram . |
| 505,382 | 9/1893 | Berghoff . |
| 694,325 | 2/1902 | Peer . |
| 942,583 | 12/1909 | Neeld . |
| 1,847,823 | 3/1932 | Dresser . |

(List continued on next page.)

FOREIGN PATENT DOCUMENTS

| | | |
|---|---|---|
| 1056388 | 2/1954 | France . |
| 1266539 | 10/1956 | Russian Federation . |

OTHER PUBLICATIONS

Declaration of Michael W. Long, dated Apr. 7, 1995, and accompanying Exhibits A–C.

*Primary Examiner*—Linda C. Dvorak
*Attorney, Agent, or Firm*—Knobbe, Martens Olson & Bear, LLP

[57] ABSTRACT

An adjustable orthotic device is disclosed for promoting joint mobility. The device is adjustable both in terms of the force applied to the joint and in terms of the direction that the force is applied to the joint. The device comprises a spring casing housing, a spring assembly, and a hinge strut assembly. The spring assembly is connected to a joint assembly via a cable and the hinge strut includes a worm gear comprising a worm and a worm wheel mechanically engaged within the joint assembly. The device is useful for sequentially treating flexion and extension contractures without removing the device from a joint of a patient.

18 Claims, 3 Drawing Sheets

U.S. PATENT DOCUMENTS

| | | |
|---|---|---|
| 2,410,560 | 11/1946 | Witte . |
| 2,465,585 | 3/1949 | Ganoe et al. . |
| 2,516,872 | 8/1950 | Hauser et al. . |
| 2,806,244 | 11/1957 | Bernhard . |
| 2,832,334 | 4/1958 | Whitelaw . |
| 2,934,785 | 5/1960 | Heuer . |
| 3,599,245 | 8/1971 | Blatchford . |
| 4,252,111 | 2/1981 | Chao et al. . |
| 4,340,041 | 7/1982 | Frank . |
| 4,397,308 | 8/1983 | Hepburn . |
| 4,485,808 | 12/1984 | Hepburn . |
| 4,489,718 | 12/1984 | Martin . |
| 4,493,316 | 1/1985 | Reed et al. . |
| 4,508,111 | 4/1985 | Hepburn . |
| 4,538,600 | 9/1985 | Hepburn . |
| 4,599,998 | 7/1986 | Castillo . |
| 4,614,181 | 9/1986 | Karisson . |
| 4,624,247 | 11/1986 | Ford . |
| 4,633,867 | 1/1987 | Kausek et al. . |
| 4,657,000 | 4/1987 | Hepburn . |
| 4,738,252 | 4/1988 | Friddle et al. . |
| 4,817,588 | 4/1989 | Bledsoe . |
| 4,844,057 | 7/1989 | Hoy . |
| 4,846,842 | 7/1989 | Connolly et al. . |
| 4,921,230 | 5/1990 | Thomsen . |
| 4,982,732 | 1/1991 | Morris . |
| 5,000,169 | 3/1991 | Swicegood et al. . |
| 5,036,837 | 8/1991 | Mitchell et al. . |
| 5,039,247 | 8/1991 | Young et al. . |
| 5,052,379 | 10/1991 | Airy et al. . |
| 5,092,321 | 3/1992 | Spademan . |
| 5,100,403 | 3/1992 | Hotchkiss et al. . |
| 5,116,296 | 5/1992 | Watkins et al. ............... 602/26 X |
| 5,328,446 | 7/1994 | Bunnell et al. ............... 602/26 X |
| 5,352,190 | 10/1994 | Fisher et al. ............... 602/26 |
| 5,472,410 | 12/1995 | Hamersley ............... 602/26 X |
| 5,547,464 | 8/1996 | Luttrell et al. ............... 602/26 |

ADJUSTABLE FLEXION AND EXTENSION JOINT ORTHOSES

This application is a continuation of U.S. patent application Ser. No. 08/231,131, filed Apr. 22, 1994, now U.S. Pat. No. 5,472,410.

FIELD OF THE INVENTION

This invention relates generally to orthopedic appliances. In particular, this invention relates to an adjustable orthotic useful for treating impairments in body joints including the finger, wrist, elbow, shoulder, knee and ankle.

BACKGROUND OF THE INVENTION

Orthotic brace units are designed to counteract the instabilities resulting from joint and related soft tissue injury. These devices stabilize the joint area and focus joint movement within a defined range of motion. Unwanted motion is reduced or eliminated and the defined movement permits resolution of the joint injury.

Movement at a particular joint can be lost through the development of flexion or extension contractures. Flexion contractures prevent extension of a joint and extension contractures prevent the joint from being fully flexed. These contractures and joint stiffness can result from disuse or neglect of an existing medical problem such as fractures or tears about a joint, vascular problems, neurological problems, surgeries, traumatic injury, illness or the like. Joint contractures develop after surgery, injury, or repair surgery. People develop extension and flexion contractures in any joint including the fingers, wrist, elbow, shoulder, knee and ankle.

These injuries require physical therapy. The therapist traditionally manipulates the joints, uses heat therapy, weights, or serial casting to improve mobility over a joint. This type of therapy requires multiple visits to a physical therapist. Since the therapy is applied to a patient over a visit that is relatively short in duration, the therapist often uses higher forces than what might be best for the patient in order to obtain mobility gains over the period of physical therapy. Complications may occur as a result of the use of high force for brief, repeated periods of time. Further, the gains in mobility during the physical therapy visits are partially lost during the interval between visits when the joint is no longer subjected to extension or flexion tension.

Spring-biased splints are also commonly used to treat flexion and extension contractures in addition to, or as an alternative to physical therapy sessions with a professional therapist. These devices provide a directional force at a joint. The devices provide tension at the point of flexion or extension to gently and continuously urge the joint into a wider range of motion. There are a number of spring-biased splints in the prior art. Examples of these splints are described in U.S. Pat. Nos. 4,485,808, 4,508,111, 4,538,600, 4,657,000 3,055,359, 3,928,872, and 3,799,159. These devices exert a force on a joint in a fixed direction. Some of these devices are adjustable in that the force can be increased or decreased. However, these devices are designed to treat either flexion or extension contractures separately, but not as a single device to treat both contractures. For these devices, a first device is fitted on the patient to manage a flexion contracture and a second device is fitted onto the patient to manage an extension contracture. The same shaped device can be used to treat either extension or flexion contractures; however, these devices are assembled during manufacture for either flexion or extension applications. Individuals having reduced mobility in both flexion and extension directions require two devices. These patients must be sent home with two orthotics. Insurance must cover the cost of two devices, suppliers must stock both devices and companies must manufacture two devices.

The present invention discloses an adjustable hinge splint that can accommodate both flexion and extension within a single device. Moreover, the device can be adjusted while on a patient to change from a device for promoting joint flexion to a device that promotes joint extension. This adjustment is patient directed. The patient is able to control and increase the tension on the damaged joint tissue. The device can be worn for brief periods each day, for several hours, or for longer periods, as recommended by the physician. Only one device is now needed to manage flexion and extension contractures. Patient directed management of the injury results in increased recovery rates and reduced visits to the therapist because a single device can apply tension to treat either flexion or extension contractures and either direction can be uniquely managed by the patient. This device decreases medical costs to either the patient or the insurer, shortens the time that the patient is away from the work place and as a result, decreases worker compensation costs. Further, this device can accommodate flexion and extension contractures in a variety of joints. This and other advantages of the present invention will be apparent from a review of this disclosure.

SUMMARY OF THE INVENTION

This invention discloses an orthotic device for promoting mobility at a joint. The patient is able to adjust the tension that the device exerts at a given joint. In addition, the force that the device applies to a joint is adjustable in either the flexion or the extension direction. Thus, a single device can be used to accommodate both flexion and extension contractures and the device can be adjusted while on the patient to sequentially promote both extension and flexion.

The present invention relates to an adjustable orthotic device for promoting mobility at a joint comprising; a spring casing, an adjustable joint assembly, and a hinge strut assembly. The spring casing comprises a housing, at least one tension inducor affixed to the housing and at least one cable, having one or more strands and having a first and second end wherein the first end is affixed to the tension inducor.

The adjustable joint assembly is rotatably connected to the spring casing. The joint assembly comprises a pulley affixed to a wheel, wherein the second end of the cable is connected to the pulley and wherein rotation of the pulley positions the cable along the circumference of the pulley in either a clockwise or a counterclockwise direction.

The hinge strut assembly is affixed to the joint assembly. The hinge strut assembly comprises a hinge strut, a drive mechanism, an adjustor and means for attaching the hinge strut to the limb of a patient. The drive mechanism is mechanically engaged with the wheel and the hinge strut assembly pivots relative to the spring casing. Rotation of the drive mechanism permits a change in the angular relationship between the pulley and the hinge strut assembly, effectively adjusting both the magnitude and the direction of the tension applied by the tension inducor to the hinge strut.

In a particularly preferred embodiment of this invention, the drive mechanism is a worm gear assembly comprising a worm and a worm wheel. More preferably the drive mechanism is directly engaged with the wheel, but it is also contemplated within the scope of this invention that the drive mechanism is indirectly engaged with the wheel. In a preferred embodiment of this invention, the pulley is facially juxtaposed to the wheel.

In another particularly preferred embodiment of this invention the device further comprises at least one cable guide positioned between the tension inducor and the pulley. Preferably, the cable guide comprises two pulleys centrally aligning the cable within the spring casing. The cable is preferably flexible.

Further, in one embodiment of this invention, the tension inducor is a spring assembly, consisting essentially of at least one coiled spring. In one embodiment the spring is an extension spring, preferably three coiled springs, and in another the spring is a compression spring.

It is contemplated that the device further comprises a limb tension support affixed to the hinge strut and attachment means to attach the spring casing to a limb of a patient. Alternatively, it is contemplated that the hinge strut is adapted to support a lower leg and apply tension to a knee joint of a patient. In another embodiment, the hinge strut is attached to a limb tension support adapted to support a forearm and apply tension to an elbow joint of a patient. In yet another embodiment the hinge strut is attached to a limb tension support adapted to support a hand and apply tension to a wrist joint of a patient. In a further embodiment, the hinge strut is attached to a limb tension support adapted to support a foot and apply tension to an ankle joint of a patient. Alternatively, it is contemplated that the hinge strut is attached to a limb tension support adapted to support a finger and apply tension to a finger joint of a patient.

In one embodiment the spring casing is proximal to the hinge strut when the device is positioned on a patient and in another, the spring casing is distal to the hinge strut when the device is positioned on a patient. Preferably the angular relationship between the pulley and the hinge strut may be sufficiently changed to reverse the angular direction of tension applied to the hinge strut.

In another aspect of this invention, an adjustable orthotic device is provided for promoting mobility at a joint comprising a tension inducor, a joint assembly and a hinge strut capable of generating force to treat a flexion or an extension contracture, wherein the orthotic device is capable of sequentially providing extension force and flexion force while positioned at a synovial joint on a patient.

In yet another aspect of this invention, a method is provided for promoting mobility at a joint comprising: attaching an adjustable orthotic device to a limb tension support wherein the adjustable orthotic device comprises a spring casing, an adjustable joint assembly and a hinge strut assembly. The spring casing comprises a housing, at least one tension inducor affixed to the housing and at least one cable having a first and second end, wherein the first end is affixed to the tension inducor. The adjustable joint assembly is rotatably connected to the spring casing and the joint assembly comprises a pulley affixed to a wheel wherein the second end of the cable is connected to the pulley and wherein rotation of the pulley positions the cable along the circumference of the pulley in either a clockwise or a counterclockwise direction. The hinge strut assembly is affixed to the joint assembly and the hinge strut assembly comprises a hinge strut, a drive mechanism, an adjustor, and means for attaching the strut to the limb of a patient. The drive mechanism is mechanically engaged with the wheel, wherein the hinge strut pivots relative to the spring casing.

The method further comprises affixing the device to the joint of a patient wherein the spring casing is positioned on a first side of the joint and the hinge strut is positioned on the opposite side of the joint, essentially paralleling the limb of a patient, and wherein the limb tension support exerts pivotal force on the joint.

In one embodiment of this invention the limb tension support is the hinge strut. In a preferred embodiment of this invention, the drive mechanism is a worm gear assembly comprising a worm and a worm wheel. In one embodiment the spring casing is positioned proximal to the hinge strut when the device is positioned on a patient. In another preferred embodiment, the spring casing is positioned distal to the hinge strut when the device is positioned on a patient.

It is contemplated that in one embodiment of this invention the limb tension support exerts force to treat a flexion contracture and in the same embodiment, the direction of the force is modified such that the limb tension support exerts force to treat an extension contracture.

In yet anther aspect of this invention, a method for promoting mobility at a joint in both the flexion and extension directions is provided, comprising attaching an adjustable orthotic device to a limb tension support, wherein the adjustable orthotic device comprises a spring casing, an adjustable joint assembly and a hinge strut assembly. Wherein the spring casing comprises a housing, at least one tension inducor affixed to the housing and at least one cable having a first and second end, wherein the first end is affixed to the tension inducor. The adjustable joint assembly is rotatably connected to the spring casing, the joint assembly comprising a pulley affixed to a wheel, wherein the second end of the cable is connected to the pulley and wherein rotation of the pulley positions the cable along the circumference of the pulley in either a clockwise or a counterclockwise direction. The hinge strut assembly is affixed to the joint assembly and the hinge strut assembly comprises a hinge strut, a drive mechanism, at least one adjustor and means for attaching the strut to the limb of a patient. The drive mechanism is mechanically engaged with the wheel, wherein the hinge strut pivots relative to the spring casing.

The method additionally comprises the step of rotating the pulley until the cable is positioned in a clockwise direction relative to the spring casing, adjusting the drive mechanism to apply the desired force to the limb tension support in a first direction, and affixing the device to the joint of a patient, wherein the spring casing is positioned on the one side of the joint and the hinge strut is positioned on the opposite side of the joint and wherein the limb tension support exerts force on the joint in the first direction and thereafter adjusting the drive mechanism, thereby rotating the pulley relative to the hinge strut until the cable is positioned in a counterclockwise direction relative to the spring casing such that the limb tension support exerts force on the joint in the second direction.

In a preferred embodiment, the drive mechanism is a worm gear assembly comprising a worm and a wormwheel. In another preferred embodiment, the limb tension support is the hinge strut and the hinge strut assembly has two adjustors. Preferably the limb tension support exerts force in the first direction to treat a flexion contracture and in the second direction to treat an extension contracture. Alternatively, the limb tension support of the same device exerts force in the first direction to treat an extension contracture and in the second direction to treat a flexion contracture.

DETAILED DESCRIPTION OF THE INVENTION

The present invention is useful for promoting mobility at a joint. In particular, the device is useful for providing force in a first direction at a joint to treat a flexion contracture and, after convenient tension adjustment, the same device is useful for providing force in a second direction to treat an extension contracture. For the purpose of this application, the term "contracture" refers broadly to any of several joint stiffness or shortened connective tissue related problems.

Like other orthotics, the device is compact and lightweight and can be adjusted to accommodate a range of forces exerted over a single direction. Also, like other orthotics, the device is adapted for use with a variety of limb tension supports that permit the hinge splint to be used to promote mobility at virtually any synovial joint in the body.

Unlike the prior art, the device of the present invention can be adjusted to apply a range of force over both a first and a second direction. Thus, a single device can be used to treat and promote mobility at a joint in either extension or flexion directions. The terms "proximal" and "distal" are used throughout this application to designate relative location. "Proximal" is used to describe that portion of an element of this invention that is closer to the heart of a patient when the patient has the device in position at a joint. "Distal" is used to describe that portion of the element farthest from the heart when the patient has the device in position at a joint.

Figures 1, 2:
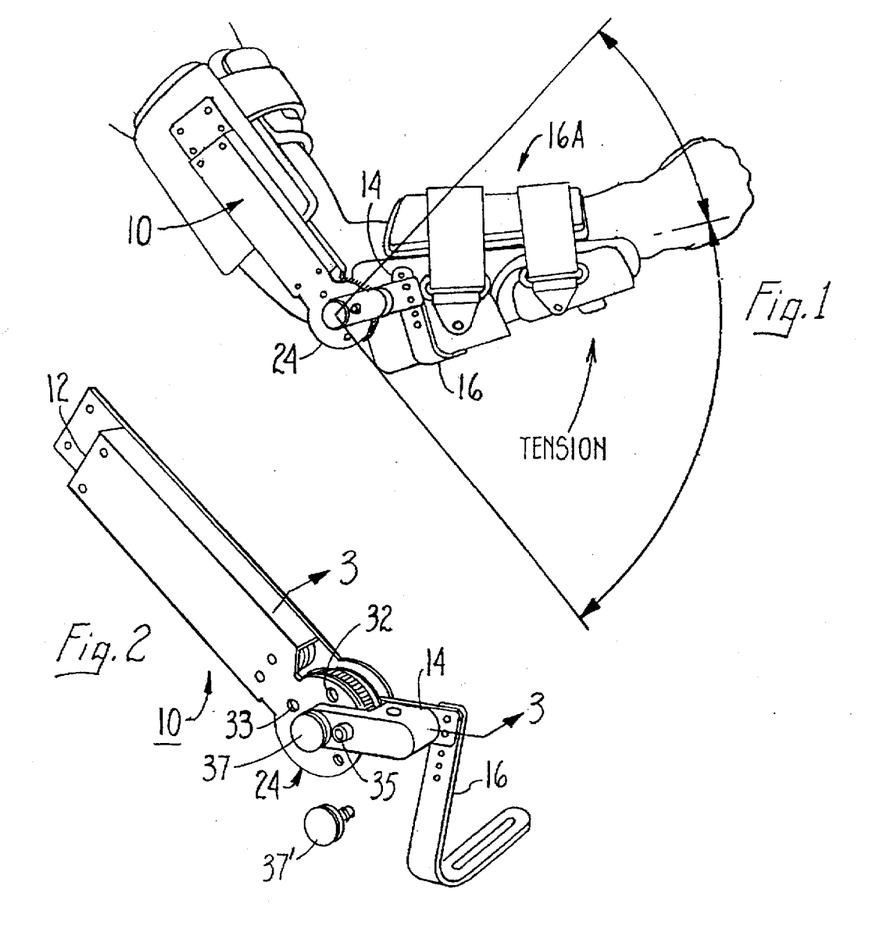
FIG. 1 is a side perspective view of the preferred elbow joint embodiment of the present invention positioned on the right arm of a patient in need of flexion or extension therapy.
FIG. 2 is a side perspective view of the preferred device of the present invention employing a limb tension support suitable for use on the elbow joint.

A preferred embodiment of the present invention is provided in FIG. 2. The device 10 comprises a spring casing 12 operably linked to a mechanical joint assembly 24 pivotally connected to a hinge strut assembly that is optionally attached to a limb support strut 14 that is adapted to accommodate a variety of limb tension supports 16. The term "spring casing" is used throughout this application to indicate that the casing contains any number of tension-inducing means. However, there is no intention on the part of the applicant to limit the invention to a spring. Alternative tension inducing means are discussed below in association with other embodiments contemplated within the scope of this invention. In the embodiment disclosed in FIG. 4, the tension inducor comprises a spring assembly and the spring assembly further comprises coiled springs.

The preferred embodiment of FIG. 1 illustrates the device having the spring casing in a proximal direction relative to the joint assembly 24. However, it is contemplated in this invention that the tension inducor that exerts force on the joint assembly 24 may be located either proximal or distal to the joint axis. For consistency, illustration and enablement, the tension inducor is illustrated proximal to the joint axis, but the tension inducor could also be positioned distal to the joint axis.

Figure 3A:
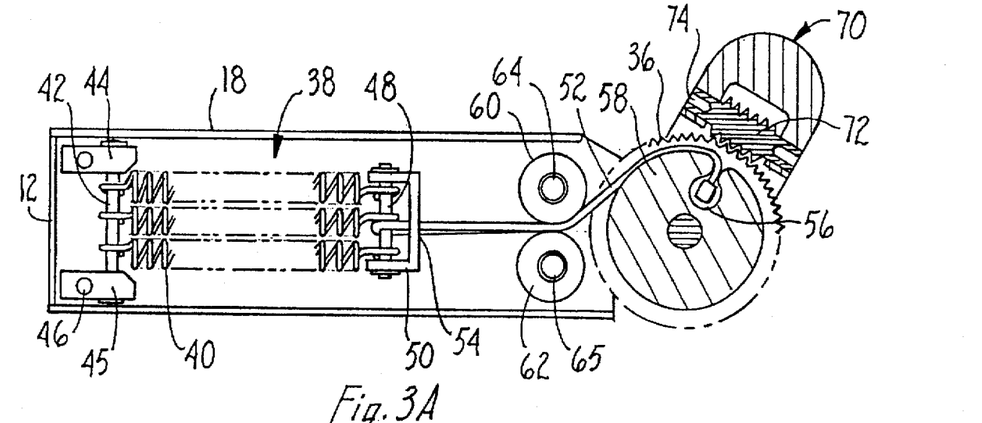
FIG. 3A is a cross-sectional view of the joint assembly of the preferred embodiment illustrating the position of the worm gear, cable, and cable pulley aligned to exert force in a first direction.
Figure 3B:
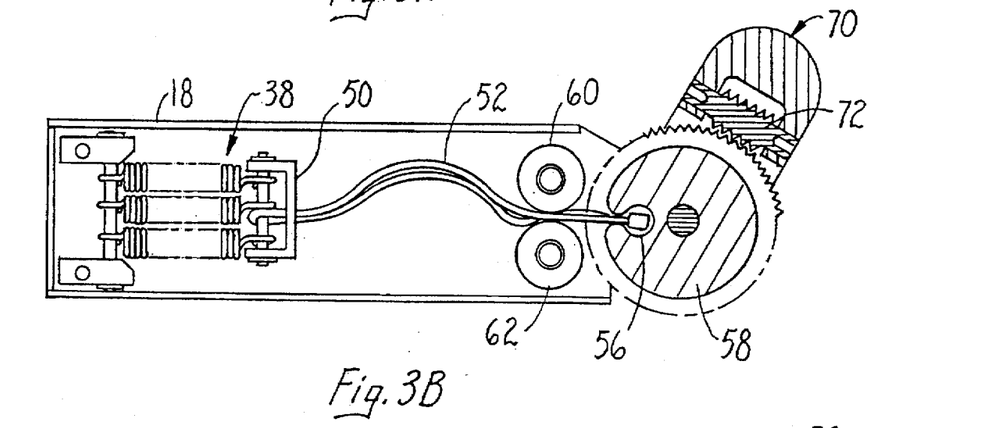
FIG. 3B is the same cross-sectional view of the joint assembly of FIG. 3A illustrating the position of the worm gear, cable, and cable pulley aligned to apply the least amount of force to the limb of a patient.
Figure 3C:
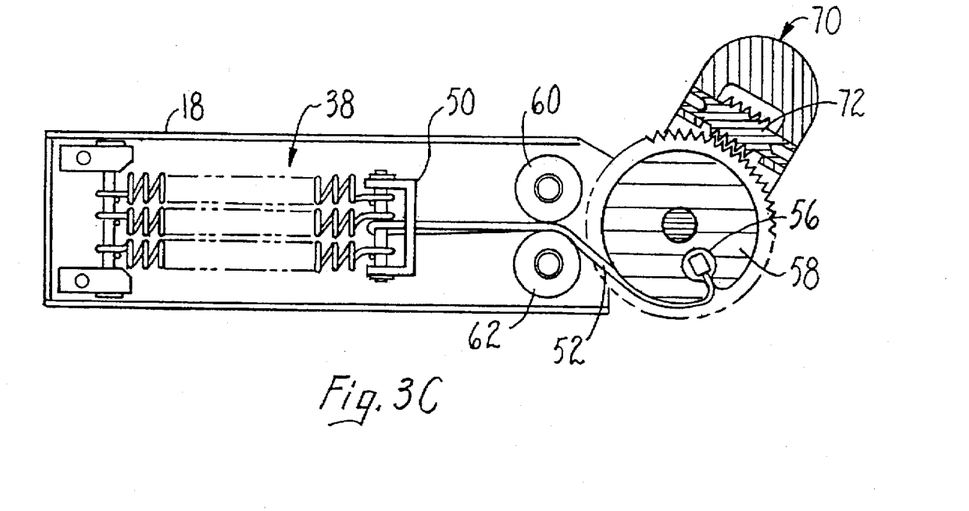
FIG. 3C is the same cross-sectional view of the joint assembly of FIG. 3A illustrating the position of the worm gear, cable, and cable pulley aligned to exert force in a second direction.
Figure 4:
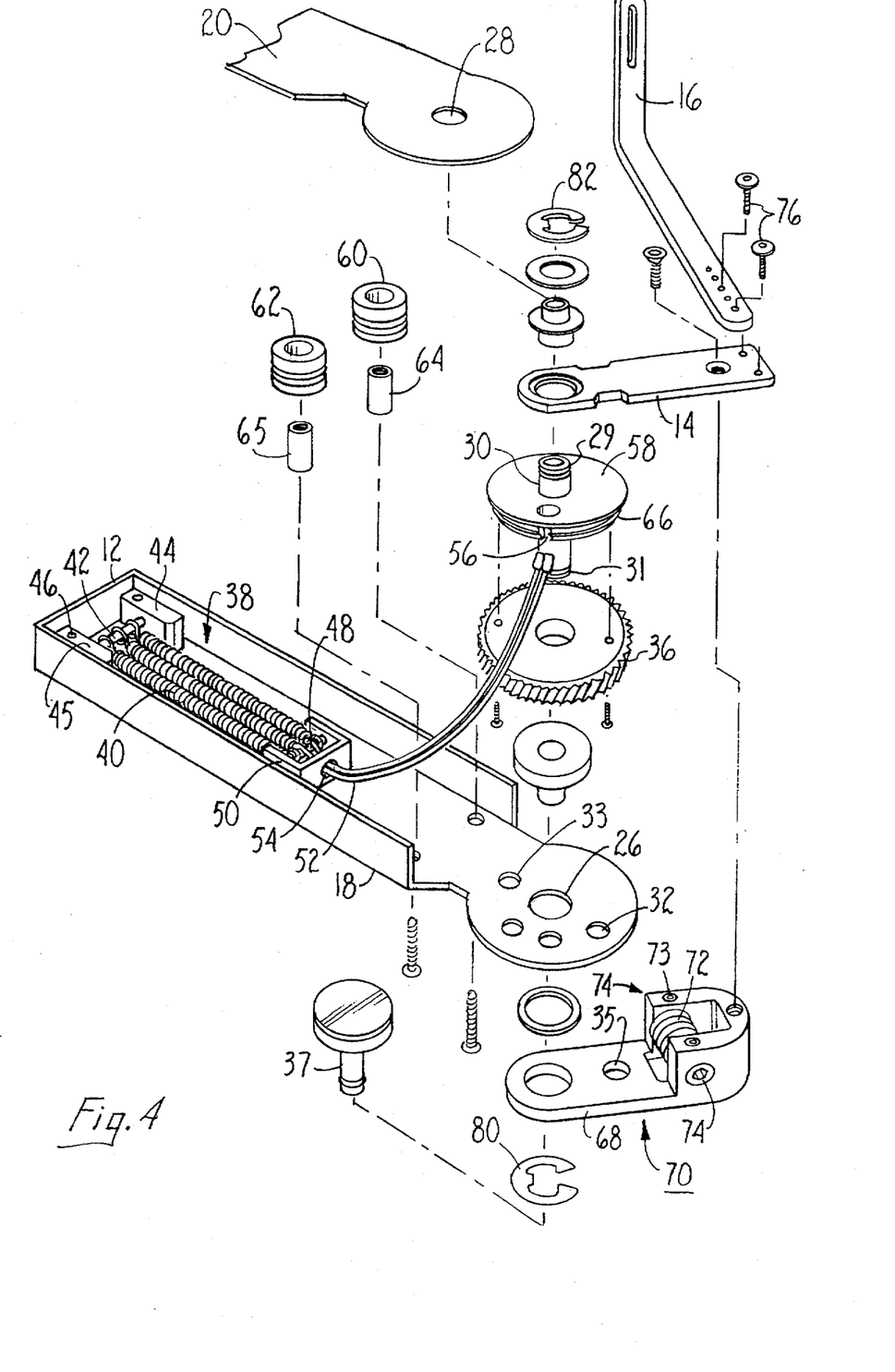
FIG. 4 is an exploded perspective view of the preferred embodiment.

Referring now to FIG. 4 which illustrates an exploded perspective view of the preferred embodiment, the spring casing 12 comprises a housing having a casing lid 18 and a casing base 20. One end of the casing lid 18 and casing base 20 are preferably contoured in a circular fashion to conform to the general shape of the joint assembly 24 (see FIG. 3). A first central aperture 26 within the casing lid 18 and a second central aperture 28 within the casing base 20 are centrally positioned at the distal ends of the casing lid 18 and the casing base 20 to accommodate a pivot axle 30. An indicia window 33 is preferably positioned along the casing lid 18 in the area of the joint assembly 24 to permit viewing of radially arranged indicia positioned on the under surface of a worm wheel 36. A series of radially arranged receiving slots 32 serve as range of motion stops for applying and removing the splint from the limb of a patient.

Locking pin 37 is positioned during use on the external face of the casing lid 18 and extends into the pivot axle 30. To rest the tension exerted by the device, locking pin 37 is removed from its storage position and inserted through any one of receiving slots 32 to lock the hinge in place. This locking mechanism facilitates the positioning and the removal of the device from the limb of a patient and provides a source of tension relief for the patient when the device is in place and exerting force on a joint. The embodiment illustrated in FIG. 4 includes three receiving slots 32 for the locking pin 37 to advantageously provide three different range of motion stops.

In the preferred embodiment of FIG. 4, the spring casing 12 houses a spring assembly 38 that is affixed to the casing lid 18 and positioned in a proximal direction relative to the joint assembly 24. The spring assembly 38 comprises at least one spring. In the preferred embodiment of FIG. 4, the spring assembly 38 comprises a plurality of springs, and more preferably three coiled springs 40. These coiled springs are available from any number of suppliers. The coiled springs employed in the embodiment of FIG. 1 are available from Associated Spring, Inc. (Part. No. EO300-055-2500, Cerritos, Calif.). In the embodiment of FIG. 4, the coiled springs 40 are connected to a first pin 42. The first pin 42 is in turn interposed between a first mounting block 44 and a second mounting block 45. In the embodiment illustrated in FIG. 4, the mounting blocks additionally contain threaded grooves 46, or other attachment means such as snap lock fittings, pins, or the like, to affix the mounting blocks 44 and 45 to the casing lid 18 and the casing base 20.

The springs 40 are connected to a spring block 50. The spring block 50 additionally houses the proximal end of a cable 52. In the preferred embodiment of FIG. 4, the coiled springs are connected at their distal end to a second pin 48 interposed between the arms of the spring block 50. In the preferred embodiment illustrated in FIG. 4, the cable 52 of FIG. 4 is comprised of a length of cable folded in half such that the proximal portion of the cable forms a loop that is preferably rotationally engaged on the second pin 48. The spring block of FIG. 4 has a centrally positioned aperture 54 to permit the cable to pass from the second pin 48, through the spring block 50. Other cables and other cable/mounting conformations are contemplated within the scope of the invention. These alternatives are discussed in detail below.

The spring block 50, as illustrated in FIG. 4, is not affixed to the spring casing 12 and is free to move longitudinally in both proximal and distal directions, relative to the mounting blocks 44 and 45, within the spring casing. In addition, the spring block 50 is free to move in a direction perpendicular to the longitudinal axis along the plane of the casing lid 18. This movement is dependent on the position of the cable 52 within the joint assembly 24.

The cable 52 is positioned and affixed at its distal end to a connector 56 on the joint assembly pulley 58. In the preferred embodiment of FIG. 4, the connector 56 is a receiving slot. The hinge device is optionally equipped with at least one cable guide. The preferred device of FIG. 4 employs two guide pulleys as cable guides. A first guide pulley 60 and a second guide pulley 62 are symmetrically positioned on either side of the central axial plane of the device (see FIG. 3). In the preferred embodiment of FIG. 4, each guide pulley is positioned on a pivot pin. The first pivot pin 64 and the second pivot pin 65 are positioned between the spring assembly 38 and the joint assembly 24. The pivot pins are affixed to the spring casing 12 by attachment screws extending from the external face of the lid 18 and base 20 into the spring casing. In the preferred embodiment illustrated in FIG. 4, the guide pulleys contain circumferential grooves adapted to receive and guide cable 52.

The joint assembly 24 (see FIG. 2) is comprised of the worm wheel 36 (see FIG. 3) affixed to a joint assembly pulley 58. The joint assembly 24 is rotatably connected to the spring casing by the pivot axle 30. In the preferred embodiment of FIG. 4, the joint assembly pulley 58 is facially juxtaposed to and affixed to the worm wheel 36. The joint assembly pulley 58 contains a connector 56 and a central aperture to accommodate the pivot axle 30. For purposes of this disclosure, the pivot post is spatially divided into a superior pivot axle 29 and an inferior pivot axle 31. Cable guide grooves 66 traverse the circumference of the joint assembly pulley 58 and serve as guides for the cable 52. Like the joint assembly pulley 58, the worm wheel 36 contains a central opening to accommodate the pivot axle 30.

The pivot axle 30, within the joint assembly 24, articulates superiorly with the hinge strut 14 and with the casing base 20. The hinge strut 14 can be adapted to engage any of several hinge strut assembly designs, as required, to accommodate a variety of limb tension supports. Similarly, limb tension supports can be positioned in any number of positions along the device as will be apparent to those skilled in the art. In the embodiment disclosed in FIG. 4, a plurality of adjustment pins 76 connect a limb tension support 16 to the device 10. The hinge strut 14 is adapted to be affixed to the worm assembly 70. Thus, the hinge strut assembly includes a hinge strut 14, a worm assembly 70 and optionally includes means for attaching the strut to a limb tension support 16. The hinge strut 14 pivots relative to the spring casing 12.

The pivot axle 30 articulates inferiorly with the casing lid 18 and with the worm gear strut 68 of the worm assembly 70. The worm assembly 70 additionally comprises a worm 72. The worm 72 is aligned laterally within the housing of the worm gear strut 68. Each base of the cylindrically shaped worm 72 articulates with a side of the worm gear strut 68 and each base of the worm 72 terminates with an adjustor 74 that preferably extends through each side of the worm gear strut 68. The preferred embodiment of FIG. 4 includes two adjustors. Multiple adjustors permit the tension to be conveniently increased or decreased when the device is positioned on a patient. The worm 72 is tangent to, and threadably engaged with, the worm wheel 36. Worm axle set screws 73 preferably have flexible tips. These set screws 73 apply pressure to alleviate axial migration of the worm 72 when under tension. A locking slot 35 is positioned on the worm gear strut such that the locking pin 37, when inserted to lock the hinge assembly in place, passes through the locking slot 35 and into one of the receiving slots 32 on the casing lid 18.

The joint assembly 24 is assembled, as illustrated in FIG. 4, over the inferior 31 and superior 29 portions of the pivot axle 30. A first circular spring clip 80 is positioned on the inferior portion 31 of the pivot axle 30 and a second circular spring clip 82 is positioned on the superior portion 29 of the pivot axle 30. Washers and sleeved washers are interposed, preferably as shown, during assembly. FIG. 4 additionally serves to illustrate the alignment of the elements of the joint assembly 24 around the pivot axle 30.

The adjustable splint device 10 can advantageously be adjusted to provide varied tension in either the flexion or the extension directions. In the preferred embodiment illustrated in FIG. 4 and in cross section in FIG. 3, rotational adjustment of the adjustor 74, such as with an allen wrench, screwdriver, socket wrench, knob, or the like, rotates the worm 72. This rotation moves the worm assembly 70 relative to the worm wheel 36 that is affixed to the pulley 58, permitting the hinge strut 14 to rotate around the longitudinal axis of the casing base 18. This movement increases or decreases the tension that is ultimately applied to the joint when it is positioned on a patient.

Referring to FIG. 3A, FIG. 3B and FIG. 3C, the joint assembly, the worm assembly 70 and the hinge strut 14 rotate relative to the spring casing 12. The device is designed to promote joint mobility in either of two modes: flexion or extension. The adjustment from flexion to extension, or extension to flexion, can be made on a patient without removing the device from the joint. When the device is positioned on the patient, rotation of the adjustor in a first direction increases the tension of the device when it is in a first mode, rotation of the adjustor in a second direction decreases the tension of the device in the first mode and with continued rotation, changes the device to provide tension in the second mode. Rotation of the adjustor in this second direction increases tension in the second mode. Rotation of the joint assembly 24, relative to the spring casing 12 moves the position of the connector 56 from one side of the spring casing to the other, lengthening or shortening the amount of cable positioned along the circumference of the pulley in either a clockwise or a counterclockwise direction relative to the proximal end of the pulley. FIG. 3A illustrates the clockwise position of the cable. FIG. 3B illustrates the position of the cable when there is the least amount of force applied to the limb of a patient. The spring is fully contracted and no tension is applied to the cable. FIG. 3C illustrates the counterclockwise position of the cable.

FIG. 1 illustrates the use of this device on the arm for treatment of an elbow joint extension contracture. Here, the hinge strut 14 is adapted with a limb tension support 16 to support the forearm. Force is exerted from the joint assembly in an upward direction to promote elbow joint flexing. The force exerted on the arm can be adjusted via the adjustor 74. Alternatively, to treat an elbow joint flexion contracture, the adjustor 74 is rotated to reposition the cable to the opposite side of pulley 58, as illustrated in FIG. 3A and FIG. 3C such that the limb tension support 14 exerts pressure downward to promote joint extension.

Figure 5:
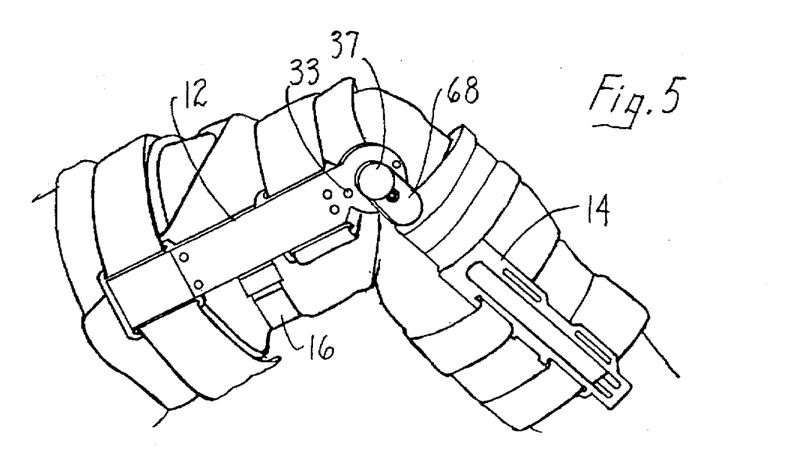
FIG. 5 is a side perspective view of the preferred knee joint embodiment of the present invention positioned on the right leg of a patient in need of flexion or extension therapy.

FIG. 5 illustrates the device of this invention adapted for use at the knee. In this embodiment, two devices 10 (see FIG. 2) are assembled as mirror images of each other and symmetrically aligned on either side of the knee joint. The soft goods include support padding and Velcro® attachment straps, or the like to secure and align the device on the knee of a patient. In this embodiment, the hinge strut 14 is lengthened relative to the elbow device. The hinge strut 14 includes attachment apertures, or the like, to secure the device to the leg. In addition, a limb tension support 16 is configured to support the thigh. Preferably, the limb tension support 16 is affixed to the proximal portion of the device 10 and in the embodiment of FIG. 5, the limb tension support 16 is affixed to the spring casings of the two aligned devices 10. It is further contemplated that the orthoses of this invention can be prepared in various sizes to accommodate both larger and smaller limbs.

It is contemplated that this device can be used at any synovial joint. Thus, it is contemplated that the device is useful for promoting mobility at the finger, wrist, elbow, shoulder, knee, and ankle. Those skilled in the art will be able to increase or decrease the size of the device, substitute the size and strength of the coiled springs and alter the sizes of the worm 72 and worm wheel 36 to create devices that are suitable for these joints. Moreover, as discussed with regard to the elbow and knee embodiments, those skilled in the art will be able to add the appropriate limb tension support and soft goods to secure the device on the limb or finger of a patient. The limb tension support can be adapted to support a forearm and apply tension to an elbow joint, or adapted to support a lower leg and apply tension to a knee joint, or adapted to support a hand and apply tension to a wrist joint, or adapted to support a finger and apply tension to a finger joint of a patient.

In addition to the exemplary limb tension supports 16 that have been discussed in this application, the art discloses a variety of limb tension supports to support fingers, hands, forearms, and legs. Therefore, it is contemplated that those in the art will be able to employ these supports in the presently claimed device without undue experimentation.

It is further contemplated that the present device can be readily modified to coexist with devices for physical therapy, or the like, to promote mobility in the larger joints of the body such as the shoulder. It is contemplated that these devices could be externally configured and affixed to the limb such as the configurations achieved using continuous passive motion machines.

The device of the present invention can be prepared from a variety of materials known in the art. Thus, the spring casing can be prepared from any durable, strong, and lightweight material such as aluminum, steel, plastics, carbon fiber, or any combination of these materials. Those skilled in the art will be able to select the appropriate material for a given application. The preferred embodiments of FIG. 1 and FIG. 5 are depicted, purely for illustration purposes, for use at the elbow or the knee joint, respectively. It is understood that the device of this invention can be positioned at any synovial joint.

It is additionally contemplated that while the embodiment of FIG. 4 employs three coiled springs, those skilled in the art will recognize that coiled springs come in various sizes and tensions. Thus, those skilled in the art can readily substitute the three springs of FIG. 4 with any number of springs, springs of different length and springs of differing tensions without undue experimentation. Alternatively a single coiled spring could be employed in the spring casing. Further, any number of springs could be incorporated into the spring casing including, but not limited to coiled extension, flat coil, or compression springs. Those skilled in the art will recognize that different methods may be required to attach the cable 52 to these other spring designs. For example, should compression springs be employed in this invention, the cable will be preferably be attached to the base of the spring, that is, that portion of the spring that is further away from the joint assembly. Moreover, as disclosed above, with regard to the spring casing 12, the term "spring casing" is used throughout this application to indicate that the casing contains any number of tension-inducing means. Thus, it is additionally contemplated that elastic members such as rubber bands, bungee cords, or the like could be positioned within the spring casing 12 to provide the tension inducor for this invention. Moreover, more elaborate means for inducing tension could be used and these include motorized devices such as servo motors or any other suitable tension-inducing means known in the art.

Moreover, it is also contemplated that there are a variety of methods known to those skilled in the art for mounting the spring assembly 38 of FIG. 4 within the spring casing 12. The methods for mounting the spring assembly 38 will depend on the type of spring assembly incorporated into the device in association with at least one cable 52, and a joint assembly pulley 58 and worm gear mechanism. It is additionally contemplated that other drive mechanisms could similarly be used in this device. For example, in another preferred embodiment of this invention, friction drives could be employed in this invention in place of the worm gear drive mechanism. These friction drives include, but are not limited to, capstan/wheel mechanisms, or the like. Further, it is contemplated that any number of threadably engaged wheels or gear chains could be interposed between the worm 72 and the pulley 58. The drive mechanism can be in direct contact with the wheel 36 or the drive mechanism can be indirectly in contact with the wheel 36. Thus, it is contemplated that the pulley of this invention is rigidly connected to the wheel and in the preferred embodiment illustrated in FIG. 4, the pulley is facially juxtaposed to the wheel 36. In this invention it is contemplated that the spring assembly, including the alternative tension-inducing means disclosed above, is distanced from the joint assembly.

The cable employed in the preferred embodiment for elbow and knee applications, as provided in FIG. 4, is a nylon coated stainless steel cable (Part No. 2050-SN-2 SAVA Industries, Inc., Riverdale, N.J.). In the embodiment of FIG. 4, the cable is folded in half and the second pin 48 is threaded through the looped end of the cable to form a double cable. The cable is threaded through the central aperture on the spring block 50. Thus, the cable attaches to the spring at the first end of the cable. It is contemplated that a single cable could similarly be employed in the present invention, and those skilled in the art will be able to attach the single cable to the second pin 48, or directly to the spring cable 40 or to the spring assembly 38, in general, through any of a variety of methods known in the art. Preferably, the double cable is coated with plastic, nylon, vinyl, teflon, or the like, to reduce friction as the cable moves within the device.

It is further contemplated within the scope of this invention that the cable 52 could be prepared from a variety of materials recognized in the art. The embodiment of FIG. 4 discloses a cable 52 that is folded over to produce a cable of double thickness. A single thickness cable has also been disclosed. This preferred cable is a filamentous cable; however, a monofilament cable is also contemplated in this invention. Cables are prepared from any number of filaments and those skilled in the art will be able to select a cable for use in the present invention without undue experimentation. It is additionally contemplated within the scope of this invention that the cable can be prepared from flexible ribbon, including, but not limited to, flexible ribbon prepared from nylon, stainless steel or copper. It is additionally contemplated that the cable 52 could be configured in a chain. Those skilled in the art will therefore realize that there are a number of different materials and that differences in cable materials do not detract from the scope of this invention.

The cable is connected at its second end to the joint assembly pulley 58 via connector 56. In the embodiment disclosed in FIG. 4, the second end of the cable 52 is crimped together with a metal fastener, or the like, and inserted into a connecting slot which serves as the connector 56. Those skilled in the art will recognize that there are any number of methods known in the art to attach the cable 52 to the joint assembly pulley and that variabilities in these methods do not detract from the scope of this invention.

As noted above, the spring block 50 of FIG. 4 is free to move either vertically or horizontally along a plane within the spring casing 12. This minimizes friction on the cable 50 and maximally aligns the spring assembly 38 with the direction of the force. It is contemplated that tracking guides could be included within the spring casing 12 to direct the movement of the spring block 50 with the direction of the cable. Cable guides prevent abrasion of the cable and prevent entanglement of the cable 50 with elements within the spring casing. In addition, guide pulleys 60 and 62 aid in transferring force from one direction to another.

This invention employs a novel application of the worm gear mechanism combined with a cable and tension-inducing means to orthotics to advantageously provide a single device with adjustable tension to treat either flexion or extension contractures. This device provides a novel orthotic that can alternate between treating flexion contractures and extension contractures without removing the device from the limb of a patient. The adjustability of the device in combination with the ability of the device to sequentially treat both flexion and extension contractures, without removing the device from a patient represents a significant improvement in the art.

While particular embodiments of the invention have been described in detail, it will be apparent to those skilled in the art that these embodiments are exemplary rather than limiting, and the true scope of the invention is that defined in the following claims.

What is claimed is:

1. A method for promoting mobility in a joint in both the flexion and extension directions, comprising the steps of:
    attaching to a limb of a patient at a joint an adjustable orthotic device, having a hinge, a strut assembly attached to said hinge and extending in a first direction therefrom, a tension inducing assembly attached to said hinge and extending away from said hinge in a second direction, such that said tension inducing assembly and said strut assembly can pivot with respect to each other, said tension inducing assembly including at least one tension inducer, and at least one force transmitting member connecting said tension inducer to said hinge;
    first applying tension through at least one said force transmitting member to a first side of said hinge to bias said hinge in a first direction; and thereafter
    adjusting the direction of the tension applied to said hinge such that tension is applied to a second side of said hinge to bias said hinge in a second direction, whereby both flexion force and extension force are individually applied to said joint.

2. The method of claim 1 wherein said tension inducer is a spring.

3. The method of claim 1, wherein said force transmitting member is flexible.

4. The method of claim 3, wherein said hinge includes a pulley attached thereto that is freely rotatable with respect to said tension inducing assembly and ordinarily fixed with respect to said strut assembly, and said tension is applied in said first applying step tangent to one side of said pulley to apply rotational force thereto in said first direction, and is applied after said adjusting step tangent to the opposite side of said pulley to apply rotational force thereto in said second direction.

5. The method of claim 1, wherein said force transmitting member is a cable.

6. The method of claim 1, further comprising the step after said first applying step of rotating an adjuster to release tension from said tension inducer on one side of said hinge and to apply a selectable amount of tension from said springs to the other side of said hinge.

7. The method of claim 1, in which said tension inducing assembly comprises a spring casing.

8. A method for promoting mobility in a joint in both the flexion and extension directions, comprising the steps of:
    attaching to a limb of a patient at a joint an adjustable orthotic device comprising
      a) a hinge;
      b) a strut assembly connected to said hinge and extending away from said hinge in a first direction;
      c) a tension inducing assembly attached to said hinge and extending away from said hinge in a second direction such that said tension inducing assembly is pivotally connected through said hinge to said strut assembly, said tension inducing assembly comprising at least one tension inducer, wherein said tension inducer generates a tension force;
      d) at least one force transmitting member in communication with said tension inducers, wherein said transmitting members transmit said force to said hinge;
      e) a force directing member, said force directing member directing said force applied to said hinge in either the flexion or extension direction;
      f) an adjuster which engages said force directing member, wherein said adjuster regulates the amount of said force applied to said hinge and determines the direction in which said force directing member directs said force;
    adjusting said adjuster to apply a selected amount of said force in a first direction, said first direction being either the flexion or extension direction; and thereafter
    adjusting said adjuster to apply a selected amount of said force in a second direction, said second direction being the alternative which was not selected as the first direction, whereby both flexion force and extension force are individually applied to said joint.

9. The method of claim 8, wherein said tension inducer is a spring.

10. The method of claim 8, wherein said force transmitting member is flexible.

11. The method of claim 8, wherein said force transmitting member is a cable.

12. The method of claim 8, wherein said force directing member is in direct communication with said tension inducers.

13. The method of claim 8, wherein said force directing member is in indirect communication with said tension inducers.

14. The method of claim 8, wherein said adjuster controls the direction in which force is applied by rotating said force directing member.

15. The method of claim 8, wherein said hinge includes a pulley attached thereto that is freely rotatable with respect to said tension inducer assembly and ordinarily fixed with respect to said strut assembly, wherein said pulley is engaged to said force transmitting member, and said force is applied in said first applying step tangent to one side of said pulley to apply rotational force thereto in said first direction and is applied in said second applying step tangent to the opposite side of said pulley to apply rotational force thereto in said second direction.

16. The method of claim 8, wherein said hinge includes a pulley attached thereto that is freely rotatable with respect to said tension inducer assembly and ordinarily fixed with respect to said strut assembly, wherein said pulley is engaged to said force transmitting member, and said force is applied in said first applying step tangent to one side of said pulley to apply rotational force thereto in said first direction and is applied in said second applying step tangent to the opposite side of said pulley to apply rotational force thereto in said second direction.

17. The method of claim 16, wherein said pulley is affixed to a wheel.

18. The method of claim 8, in which said tension inducing assembly comprises a spring casing.

* * * * *

UNITED STATES PATENT AND TRADEMARK OFFICE
CERTIFICATE OF CORRECTION

PATENT NO. : 5,683,353
DATED : November 4, 1997
INVENTOR(S) : Greg A. Hamersly

It is certified that error appears in the above-identified patent and that said Letters Patent is hereby corrected as shown below:

In column 12, line 21, please delete "springs", and insert therefor --"tension inducer".

Signed and Sealed this

Seventh Day of March, 2000

Attest:

Q. TODD DICKINSON

*Attesting Officer*   *Commissioner of Patents and Trademarks*